US011519721B2

(12) United States Patent
Van Der Mark et al.

(10) Patent No.: US 11,519,721 B2
(45) Date of Patent: Dec. 6, 2022

(54) OPTICAL SHAPE SENSOR, OPTICAL SHAPE SENSING CONSOLE AND SYSTEM, AND OPTICAL SHAPE SENSING METHOD

(71) Applicant: KONINKLIJKE PHILIPS N.V., Eindhoven (NL)

(72) Inventors: Martinus Bernardus Van Der Mark, Best (NL); Anna Hendrika Van Dusschoten, Eindhoven (NL); Eibert Gerjan Van Putten, 'S-Hertogenbosch (NL); Gert Wim 'T Hooft, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 159 days.

(21) Appl. No.: 16/964,220

(22) PCT Filed: Jan. 24, 2019

(86) PCT No.: PCT/EP2019/051674
§ 371 (c)(1),
(2) Date: Jul. 23, 2020

(87) PCT Pub. No.: WO2019/149600
PCT Pub. Date: Aug. 8, 2019

(65) Prior Publication Data
US 2021/0041227 A1    Feb. 11, 2021

(30) Foreign Application Priority Data
Jan. 30, 2018   (EP) .................................. 18154130

(51) Int. Cl.
G01B 11/24    (2006.01)
G02B 6/02     (2006.01)
(Continued)

(52) U.S. Cl.
CPC .......... *G01B 11/24* (2013.01); *G02B 6/02042* (2013.01); *G02B 6/2552* (2013.01);
(Continued)

(58) Field of Classification Search
CPC ................ G01B 11/24; G01B 9/02057; G02B 6/02042; G02B 6/2552; G02B 6/262;
(Continued)

(56) References Cited

U.S. PATENT DOCUMENTS

| 10,299,661 B2 | 5/2019 | Van Putten |
| 2008/0131052 A1* | 6/2008 | Matsumura ......... G02B 3/0087 385/33 |

(Continued)

FOREIGN PATENT DOCUMENTS

| CN | 107124867 A | * | 9/2017 | ............. A61B 34/10 |
| CN | 103328922 B | * | 10/2017 | ............. A61B 34/20 |

(Continued)

OTHER PUBLICATIONS

International Search Report and Written Opinion dated Apr. 23, 2019 for International Application No. PCT/EP2019/051674 filed Jan. 24, 2019.

*Primary Examiner* — Michael A Lyons

(57) ABSTRACT

An optical fiber (F2) having a length defining a longitudinal direction is disclosed. The optical fiber (F2) has at least two fiber cores (C21, C22) extending along the length of the optical fiber (F2), and an optical coupling member (OCM2) is arranged at a proximal optical fiber end of the optical fiber (F2). The coupling member (OCM2) has a first distal end face (OF2) optically connected to the proximal optical fiber end, and a proximal second end face (IF2) spaced apart from the first distal end face (OF2) in the longitudinal direction of
(Continued)

the optical fiber (F2), the optical coupling member (OCM2) being configured to couple light into each of the fiber cores (C21, C22, C23).

14 Claims, 6 Drawing Sheets

(51) Int. Cl.
  *G02B 6/255* (2006.01)
  *G02B 6/26* (2006.01)
  *G02B 6/32* (2006.01)
  *A61B 5/00* (2006.01)
(52) U.S. Cl.
  CPC ............... *G02B 6/262* (2013.01); *G02B 6/32* (2013.01); *A61B 5/6851* (2013.01); *A61B 2562/0266* (2013.01)

(58) Field of Classification Search
  CPC ...... G02B 6/32; G01D 5/353; G01D 5/35306; G01D 5/35316
  See application file for complete search history.

(56) References Cited

U.S. PATENT DOCUMENTS

| | | | |
|---|---|---|---|
| 2016/0213432 A1* | 7/2016 | Flexman | A61B 5/065 |
| 2016/0231104 A1* | 8/2016 | Ramachandran | A61B 34/20 |
| 2016/0374562 A1 | 12/2016 | Vertikov | |

FOREIGN PATENT DOCUMENTS

| | | |
|---|---|---|
| EP | 2319388 | 5/2011 |
| JP | 2008052284 | 3/2008 |
| WO | 2011056187 | 5/2011 |
| WO | 2016/193051 | 12/2016 |

\* cited by examiner (A)

(B)

OPTICAL SHAPE SENSOR, OPTICAL SHAPE SENSING CONSOLE AND SYSTEM, AND OPTICAL SHAPE SENSING METHOD

CROSS REFERENCE TO RELATED APPLICATIONS

This application is the U.S. National Phase application under 35 U.S.C. § 371 of International Application No. PCT/EP2019/051674 filed Jan. 24, 2019, published as WO 2019/149600 on Aug. 8, 2019, which claims the benefit of European Patent Application Number 18154130.1 filed Jan. 30, 2018. These applications are hereby incorporated by reference herein.

FIELD OF THE INVENTION

The present invention relates to the field of optical shape sensing. The invention finds applications in interventional medical devices and interventional treatment procedures, in particular in minimally invasive medical procedures using optical interrogation techniques.

BACKGROUND OF THE INVENTION

In minimally invasive medical interventions, guidewires are used for advancing catheters to a target region (e.g., a guidewire for advancing a catheter to a heart during a minimally invasive cardiovascular intervention). These procedures are generally guided with, for example, real-time X-ray imaging, which depicts two-dimensional projection images of the catheters and guidewires. However, challenges with X-ray imaging include the 2D nature of the imaging and the ionizing radiation, which may be harmful to the patient and physician, as well as the contrast agent that is toxic to the patient's kidneys. A more viable alternative is using optical shape sensing technology, which may provide full three-dimensional shape information of medical devices without the need for any harmful radiation. One way to implement spatially sensitive bend and twist sensing using optical fibers is to combine multiple cores having fiber-Bragg gratings along their length. One potential set-up may be three or more fiber cores oriented in a helical structure along the longitudinal fiber axis including an additional straight fiber core in the helix center.

Specifically, optical shape sensing guidewires are used in minimally invasive procedures that have optical connectors for facilitating a backloading of catheters over a proximal end of the guidewires. The guidewire may be advanced to a target region of the intervention prior to the introduction of the diagnostic or therapeutic catheter. The guidewire is typically a thin wire that allows loading of the catheter over a proximal end of the guidewire and an advancement of the catheter over the guidewire to reach the target region.

In order to allow backloading, optical connectors for guidewires are required which are small enough to allow standard catheters to be backloaded onto the guidewire prior to re-establishing the optical connection of the shape sensing enabled guidewire with the optical shape sensing console.

For backloadable guidewires, optical connectors have been proposed which comprise one or more graded-index (GRIN) lenses, as, for example, described in WO 2016/193051 A1. GRIN lenses are a promising choice as optical coupling members in optical connectors because of their compactness and their intrinsically low surface reflection. In a conventional lens, the combination of the curved surfaces at any point on the surface and the refractive index of the lens material cause the light to refract in a desired direction at the given point. The refractive index difference, usually between the glass material of the lens and the surrounding air, is essential to the working of a conventional lens, but as a disadvantage it also causes some of the incident light to be reflected. In a GRIN lens, contrary to a conventional lens, the light beam is bent due to a refractive index profile of the lens, which varies in the radial direction. The working of the GRIN lens is hence not crucially dependent on the refractive index difference between lens material and any adjacent material along the optical path at input or output of the GRIN lens. This property is used to eliminate, or at least highly suppress, reflections in the optical path by avoiding any air to glass transitions when the connection between two optical connectors is established. Low reflection is achieved when the refractive index is closely matched at any point along the optical path. The reflection should be made low because otherwise it will overwhelm the relatively weak optical response signals coming from each point along the sensing optical fiber during the shape sensing procedure.

One characteristic of GRIN lenses is the so-called pitch. A light beam entering the GRIN lens is continuously refracted due to the refractive index profile in the radial direction of the GRIN lens, and the optical field inside the GRIN lens is therefore periodically changing along the light propagation axis with a period length. The pitch of the GRIN lens is defined as the geometrical length of the GRIN lens divided by the period length. For example, if the pitch is ¼, or ¾, or ⁵⁄₄ etc., a set of collimated beams may exit the GRIN lens at the output end facet, when light beams enter the GRIN lens from the fiber cores of the optical fiber at the input end facet, and vice versa. When a GRIN lens shall have a predetermined pitch, then the geometric length of the GRIN lens is fixed based on the refractive index in the axial center of the GRIN lens and the numerical aperture of the GRIN lens.

In optical shape sensing (OSS), strains are measured in e.g. four cores of an optical fiber sensor, and from these measurements the 3D shape of the sensor is calculated. To define a starting position for the 3D shape reconstruction of the sensor, some method is required to align the relative shape reconstruction starting positions of all of the fiber cores of the multi-core sensing fiber down to the micron level. One possibility is to use a correlation method that uses the reflections from fiber-Bragg gratings or Rayleigh backscattering in the fiber. The method compares the present state of backscattering with previously recorded reflection profiles from perhaps several millimeters of fiber, as a calibration. Another method employs the reflection at a refractive index step, for example at a connector interface, in particular when the connector is polished at right angles. The refractive index step occurs at exactly the same position for all cores, which is a very useful property because it is independent of a calibration method. It would be logical to use this principle also for the connection of a backloadable guidewire, i.e. to use the refractive index step at the interface between the guidewire connector lens and the patch cord connector lens as the starting point for shape reconstruction. However, there are some problems with this approach. One problem is caused by the necessity to have a sterile barrier, e.g. a foil, between the two connector ends of patch cord and guidewire, introducing two refractive index steps with two reflections at short distance (short time delay) which cannot be accurately be separated. Another problem occurs during the reconnection of a guidewire, in particular after unloading a catheter back over the connector. The connector will become contaminated, or at least wet which alters the refractive index step and thus the intensity of the reflection at this interface. Yet another problem is that any reconnection of the backloadable guidewire will show a slightly different compression of the intermediate layer, e.g. a foil that forms the sterile barrier, which again alters the reflection. Thus, the refractive index step at the interface between the two connectors is variable, rendering identification of this interface in the optical response signals from the fiber cores difficult and shape reconstruction of the shape sensor less accurate.

The aim of this invention is to accurately measure time delays in signals in a number of channels (fiber cores) simultaneously, down to the level of micrometers of light propagation delay. By using a suitable physical marker such as a refractive index step common to all markers, the delays between signals in channels can be found and corrected for. In each separate channel, there are other reflections that may disturb and lead to a systematic or random error on the measured delays as a result of cross talk. Although any of the reflections may be very sharp in the time domain, the measurement is done in discrete steps and a finite sampling-range Fourier transform is performed. This broadens the reflection peak in the time domain, and the tails of those peaks originating from different reflections may start to overlap, leading to cross talk in the measurement between the given reflections. A typical step length may be 0.05 mm and a typical sampling range may contain 64 steps (nodes), corresponding to an interval of 3.2 mm.

On top of intra-channel cross talk explained above, there may as well be inter-channel cross talk, which must be taken into account similarly. Such cross talk is the result of optical coupling between different channels caused by imperfections in the optics.

SUMMARY OF THE INVENTION

It is an object of the present invention to provide an optical shape sensor that allows shape reconstruction with improved accuracy.

It is a further object of the invention to provide an optical shape sensing console configured to reconstruct the shape of the optical shape sensor such with improved accuracy.

Further, it is an object of the present invention to provide an optical system comprising the optical shape sensor and the optical shape sensing console.

It is a further object to provide a method of optical shape sensing which allows shape reconstruction with improved accuracy.

According to a first aspect of the invention, an optical shape sensor is provided, comprising an optical fiber having a length defining a longitudinal direction, the optical fiber having at least two fiber cores extending along the length of the optical fiber, an optical coupling member arranged at a proximal optical fiber end of the optical fiber, the coupling member having a first distal end face optically connected to the proximal optical fiber end, and a proximal second end face spaced apart from the first end face in the longitudinal direction of the optical fiber, the optical coupling member being configured to couple light into each of the fiber cores, an optical interface at a transition from the optical coupling member to the proximal optical fiber end, the optical interface being partially reflective and substantially transmissive, wherein the optical interface is arranged in such a distance distally from the second end face and configured such that light is reflected at the optical interface with a reflection intensity distribution which substantially does not overlap in time with a reflection intensity distribution of light reflected at the second end face of the optical coupling member.

The invention is based on the idea to provide an optical interface with a refractive index step in the optical shape sensor at a location of the transition from the optical coupling member to the proximal optical fiber end. This optical interface may be advantageously used as a starting position for all fiber cores for shape reconstruction. Differently from the optical interface at the proximal end of the optical coupling member, i.e. at the interface between the optical shape sensor connector and a patch cord counter connector, the optical interface at the fiber/coupling member-transition is not subject to influences from a sterility barrier, pressure between the two connectors and the like. Thus, reflections at this interface are stable and can be easily recovered in the optical response signals from all the fiber cores. Time positions of light reflections at this optical interface in the optical response signals of the fiber cores may be reliably measured, and the time delay in the response signals of the fiber cores may be adjusted to zero so that the relative starting positions of all of the fiber cores of the optical fiber may be accurately aligned down to the micron level. The optical interface at the transition from the optical coupling member to the proximal optical fiber end is partially reflective, e.g. may provide a reflection of less than −50 dB, and is substantially transmissive, e.g. an insertion loss at the optical interface may be less than 1 dB. Further according to the invention, the optical interface is sufficiently spaced apart from the proximal end face of the optical coupling member so that the reflection intensity distribution of light reflected at the transition from the fiber to the coupling member substantially does not overlap in time with the reflection intensity distribution of light reflected at the proximal end face of the coupling member. "Substantially" also includes that there is no overlap at all, but may include a small negligible overlap so that light reflections from the optical interface at the fiber/coupling member-transition are well recognizable and a suitable choice for the starting position of shape reconstruction.

The distance of the optical interface at the fiber/coupling member-transition from the proximal end face of the coupling member may be in a range of 1 mm-5 mm or more. In this configuration, the reflection intensity peaks of reflections at the fiber/coupling member-transition are sufficiently separated in the time domain from the reflection intensity peaks of reflections at the proximal end face of the optical coupling member. Simply speaking, if for example, at a certain intensity level of reflection, the Fourier transform requires 64 nodes of 0.05 mm to determine the reflection peak position accurately to the micron, then the coupling member end faces should be at least 3.2 mm apart.

Further, the optical interface at the transition from the optical coupling member to the proximal optical fiber end should be configured such that its light reflection is not only sufficiently separated in the time domain from other measured input light reflections, but also itself of sufficient intensity and, therefore, well recognizable. This can be achieved by reducing the reflectivity at the proximal end face of the optical coupling member and/or by increasing the reflectivity at the optical interface at the transition from the optical coupling member to the proximal optical fiber end. Increasing or decreasing the reflectivity of the optical interface may be achieved by tuning the refractive index difference at the optical interface at the transition from the optical coupling member to the optical fiber end.

On the one hand, it is key that the marker (optical interface at the transition from the optical coupling member to the proximal fiber end) reflection is higher than the shape sensing signal from the sensor, so that is clearly discernible. On the other hand, the tail of the marker reflection peak will overlap with the sensor signal. Care must be taken that the shape sensing signal from the fiber sensor is not overwhelmed by the marker reflection. Typically, it is found that a marker signal 15 dB-20 dB above the sensor signal is suitable, the sensor signal being typically more than 25 dB above the noise floor or Rayleigh scattering, and where the sensor signal is due to back reflection from fiber Bragg gratings. It should be noted, however, that the known structure of the sensor signal allows for it to be filtered away so that the marker reflection peak may become visible with a level of 30 dB-40 dB above the residual, filtered background.

Further embodiments of the optical shape sensor according to the invention will be described below.

In a preferred embodiment, the optical coupling member is a graded-index (GRIN) lens, which preferably has a pitch of k/4, wherein k is an odd integer greater than or equal to 1.

A GRIN lens as the optical coupling member is advantageous if the optical shape sensor is a backloadable optical shape sensor, for example a backloadable shape-sensing enabled guidewire. The pitch of such a GRIN lens of ¼, ¾, ⁵⁄₄, . . . , is advantageous because on the one hand the marker optical interface which forms the starting point for shape reconstruction then is sufficiently spaced apart from the proximal end face of the GRIN lens so that intensities of light reflections at the marker optical interface are well separated from intensities of light reflections at the proximal end face of the GRIN lens, and on the other hand, GRIN lenses with these pitches provide focusing of collimated beams at the proximal end face onto the proximal fiber end of the sensor optical fiber.

The GRIN lens may have a pitch of ⁵⁄₄ or ⁷⁄₄. If the GRIN lens has a pitch of ¾, ⁵⁄₄ or ⁷⁄₄, a good compromise may be found between a sufficiently large distance of the optical interface from the proximal end face of the GRIN lens on the one hand and keeping GRIN lens aberrations in a controllable range. With these pitches, the numerical aperture and radial cross section of the GRIN lens can be substantially kept the same as in case of a ¼ pitch GRIN lens. Further, in the range of pitches of the GRIN lens mentioned above, mechanical strength of an optical connector having the GRIN lens may be still high even when taking into consideration the very small diameter of the GRIN lens in a backloadable version of the optical shape sensor. A typical diameter may be 0.2 mm-0.4 mm.

It is of further importance that a gradient-index transition layer may be formed as a result of a fusion-splicing process in which the glass material of lens and fiber are joined. The thickness of this layer may typically be 10 nm-100 nm, or even more, depending on the exact procedure. A layer of this kind will generally reduce the reflected intensity.

To good approximation, the reflection of a sharp transition between a GRIN lens of refractive index $n_0 = 1.472$ and an optical fiber with mode refractive index $n_{mode} = 1.451$ is given by:

$$R \approx \left(\frac{n_0 - n_{mode}}{n_0 + n_{mode}}\right)^2$$

For the given values this leads to a reflection of $R = 5.1 \times 10^{-5}$, which is rather high for the purpose of this invention. Using the advantage of a gradient-index transition layer one can reduce the reflection further by a factor of 10-100, and in a practical situation a factor of approximately 50 is found.

A ratio of an intensity of light reflected at the optical interface (OI) to an intensity of light incident onto the optical interface (OI) may be in a range from $10^{-6}$ to $10^{-5}$.

Further, an optical transition layer refractive index of the optical interface at the fiber/coupling member-transition may be different from at least one of an optical fiber refractive index of the optical fiber and an optical coupling member refractive index of the optical coupling member.

In this embodiment, light reflections at the marker optical interface are well recognizable due to the refractive index step between the marker optical interface and the proximal optical fiber end and/or between the marker optical interface and the refractive index of the optical coupling member. For example, the optical coupling member and the optical fiber may have the same or substantially the same refractive index, wherein in this case the marker optical interface may be provided by a thin material layer between the optical fiber end and the distal optical coupling member end which has a refractive index different from the refractive indices of the optical fiber material and the optical coupling member material. This can be achieved, for example, by using an adhesive or glue having a refractive index different from the refractive indices of the optical fiber and the optical coupling member. In another example, the optical fiber may have a refractive index which differs from the refractive index of the optical coupling member wherein in this case the optical fiber end may be fusion spliced to the optical coupling member, and the fusion splice then itself provides the refractive index step of the optical interface at the transition of the proximal optical fiber end to the distal end face of the optical coupling member.

Thus, in an embodiment, the distal first end of the optical coupling member may be fusion spliced to the proximal optical fiber end, and the optical interface is provided at the fusion splice.

In an alternative embodiment, the distal first end of the optical coupling member may be connected to the proximal optical fiber end via a glue layer, and the optical interface is provided at the glue layer.

If the proximal end face of the optical coupling member is configured to be connected to a distal end of the light supplying patch cord supplying the input light, a foil may be arranged at the proximal end face of the optical coupling member which is configured to reduce a reflection of light at the connection of the proximal end face of the optical coupling member and the distal end of the light supplying patch cord.

This measure lowers the reflection intensity of reflections at the proximal end face of the coupling member. The foil preferably is refractive-index matched with the optical coupling member on the shape sensor side and the counter optical coupling member on the patch cord side so that it further reduces the reflection intensity of reflections at the proximal end face of the optical coupling member relative to the reflection intensity of reflections at the marker optical interface at the transition from the optical coupling member to the proximal optical fiber end. As a result, the reliability of the identification of the reflection peaks of reflections at the optical interface, and thus, the accuracy of the determination of the starting point for shape reconstruction is further improved.

In particular, it is advantageous if the foil is compressible and/or elastic. A compressible foil may help in compensating for an inclination angle or curvature of the proximal end face of the optical coupling member that may be due to manufacturing tolerances. An inclination angle or curvature of the proximal end face of the optical coupling member and or of the distal end face of the counter optical coupling member may lead to refraction at the proximal end face due to an air gap which can be avoided by the compressible foil between the optical coupling member of the shape sensor connector part and the counter optical coupling member connector part.

According to a second aspect of the invention, an optical shape sensing console is provided, comprising:

an optical interrogation unit configured to transmit input light into an optical shape sensor according to the first aspect and to receive optical response signals from each of the fiber cores of the optical sensor in response to the input light, a shape reconstruction unit configured to reconstruct a shape of the optical sensor from the optical response signals, wherein the shape reconstruction unit is configured to determine a starting point for each of the fiber cores for shape reconstruction from the optical response signals, wherein the shape reconstruction unit is configured to identify a respective peak of a reflection intensity distribution of the light reflected at the optical interface in the optical response signals and to determine a starting position for shape reconstruction from said peaks.

According to this aspect of the invention, the optical shape sensing console uses peaks of the reflection intensity distribution of reflections at the optical interface at the fiber/coupling member transition in the optical response signals to determine the starting point for shape reconstruction with high accuracy. The shape reconstruction unit determines from the peaks in the optical response signals from all fiber cores the relative starting positions of the fiber cores, for example, in the time domain. The shape reconstruction unit may further align the relative starting positions in the time domain by adjusting a delay between the determined relative starting positions to zero. This may be done by using a phase recovering algorithm.

The shape reconstruction unit then may reconstruct the 3D shape of the optical shape sensor starting from the aligned starting positions of the fiber cores.

According to a third aspect of the invention, an optical shape sensing system comprising an optical shape sensor according to the first aspect and an optical shape sensing console according to the second aspect is provided.

According to a fourth aspect of the invention, a method of optical shape sensing is provided, comprising:

transmitting input light into an optical shape sensor according to the first aspect, receiving optical response signals from each of the fiber cores of the optical shape sensor in response to the input light, identifying a respective peak of a reflection intensity distribution of input light reflected at the optical interface in the optical response signals, determining a shape reconstruction starting position for each of the fiber cores from the peaks, and reconstructing a shape of the optical shape sensor starting from the shape reconstruction starting position.

According to a further aspect of the invention, a computer program comprising program code means for causing a computer to carry out the steps of the method according to the fourth aspect is provided, when said computer program is carried out on a computer.

The optical shape sensing console, the optical shape sensing system, and the method of optical shape sensing according to the invention have the same or similar advantages as indicated above with respect to the optical shape sensor. It shall be understood that the claimed method, the claimed console, the claimed system and the claimed computer program have similar and/or identical preferred embodiments as the claimed optical shape sensor, in particular as defined in the dependent claims and as disclosed herein.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
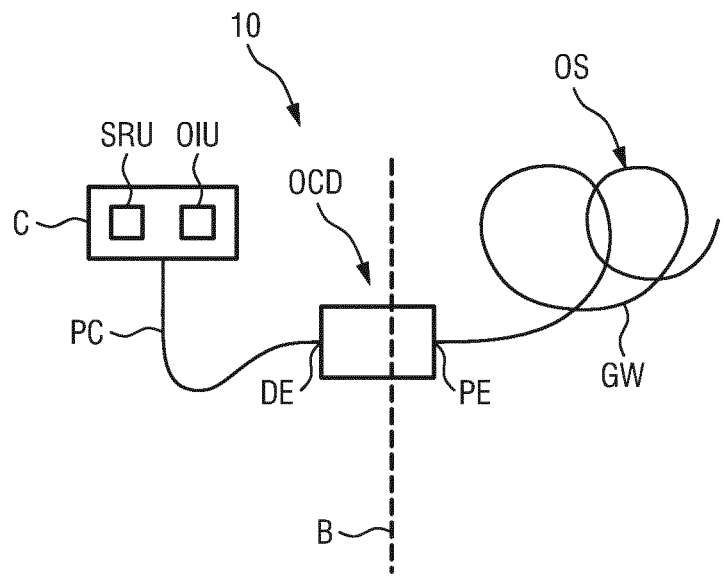
FIG. 1 shows a sketch of an optical shape sensing system comprising an optical shape sensor and an optical shape sensing console.

FIG. 1 shows an optical shape sensing system 10 that may be used for minimally invasive medical procedures. The optical shape sensing system 10 comprises an optical shape sensor OS and an optical shape sensing console C. The optical shape sensor OS may be connected to the optical shape sensing console C via a patch cord PC. The optical shape sensor OS and the patch cord PC may be connected to each other via an optical connection device OCD.

Figure 2:
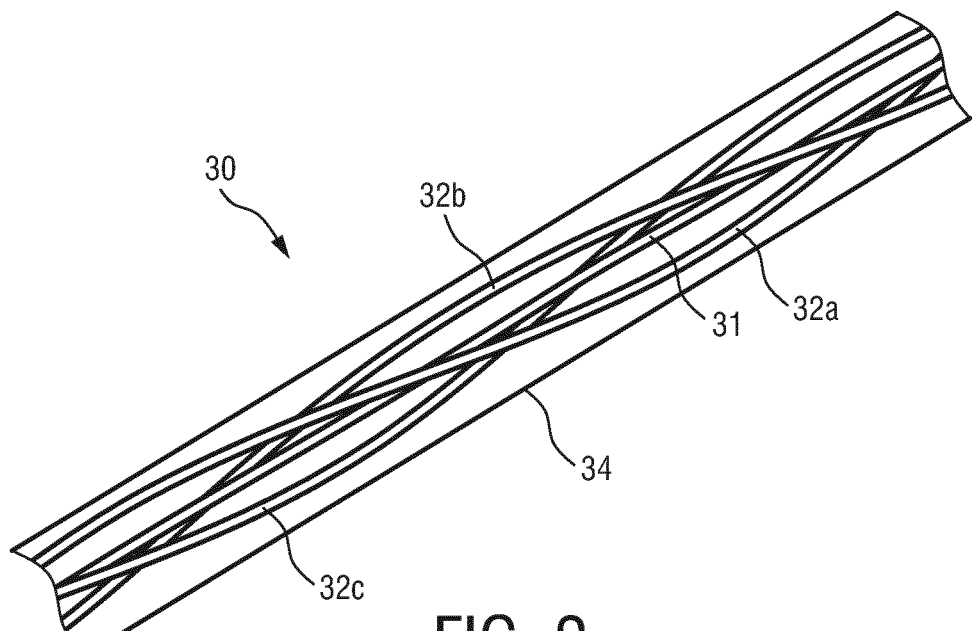
FIG. 2 shows a piece of length of an optical fiber for use in the optical shape sensor in FIG. 1.
Figure 3:
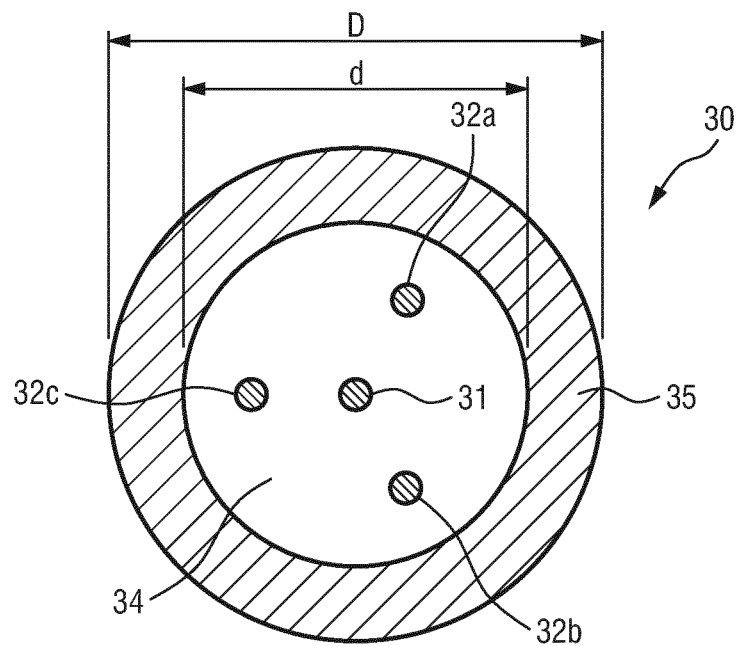
FIG. 3 shows a cross-section of the optical fiber in FIG. 2.

The optical shape sensor OS comprises an optical fiber having at least two fiber cores extending along the length of the optical fiber. An example of an optical fiber 30 for use in the optical shape sensor OS is shown in FIGS. 2 and 3. Optical fiber 30 shown in FIGS. 2 and 3 is a multi-core fiber having four fiber cores 31, 32a, 32b and 32c. The fiber core 31 is a central fiber core extending along the central axis of the optical fiber 30. Fiber cores 32a, 32b and 32c are outer cores that are helically wound around the central core 31. Each core 31, 32a, 32b, 32c may be embedded in a cladding 34. The cores 31, 32a, 32b, 32c are protected by a coating 35 (not shown in FIG. 2), for example a polymer coating. The three outer cores 32a, 32b, 32c are equidistant from each other in a cross section perpendicular to the longitudinal direction of the optical fiber 30 as shown in FIG. 3.

An outer diameter D of the coating 35 may be 200 µm. An outer diameter d of the cladding may be 125 µm. The diameter of each core 31, 32a, 32b, 32c may be 6 µm, for example. The distance between each outer core 32a, 32b, 32c and the central core 31 may be 35 µm, for example.

The fiber cores 31, 32a, 32b, 32c each may have fiber Bragg gratings along their length.

With reference to FIG. 1 again, the optical shape sensor OS may be configured as a backloadable guidewire GW. A proximal end portion PE of the guidewire GW has a functionality of being a connector part for connection with a distal end of DE of the patch cord PC. The connector part of the guidewire GW has to mate with a counter connector part of the patch cord PC. Since the guidewire GW comes into direct contact with a patient, the guidewire GW must be sterile, while the patch cord and the console C may not be sterile. The connector part of the guidewire GW and the counter connector part of the patch cord PC form the optical connection device OCD. A line B illustrates the barrier between the sterile side (guidewire GW) and the non-sterile side (patch cord PC, console C).

Figure 4:
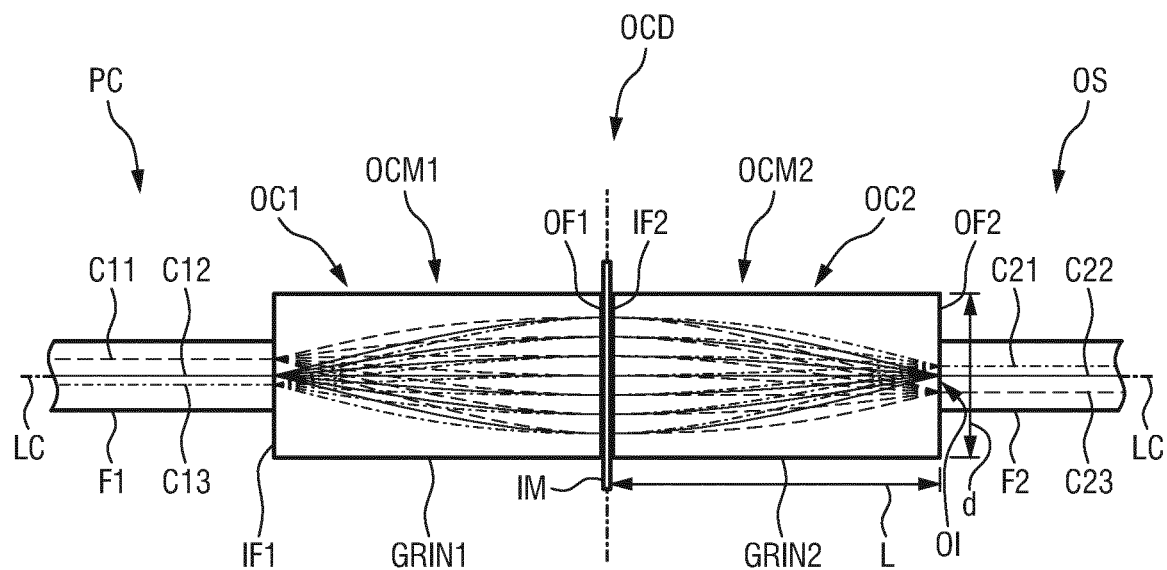
FIG. 4 shows an embodiment of an optical fiber and GRIN lens arrangement.

In the backloadable version of the guidewire GW, or in general of the optical shape sensor OS, the connection between the optical shape sensor OS and the patch cord PC relies on connector parts both of which contain an optical coupling member. The coupling member may be configured as a graded-index (GRIN) lens. An example of such an optical connection device OCD is shown in FIG. 4. FIG. 4 shows an optical connector part OC1 which may be the connector part of the patch cord PC, and an optical connector part OC2, which may be the connector part of the optical shape sensor OS in FIG. 2. The optical connector part OC2 comprises an optical coupling member OCM2 that may be configured as a GRIN lens GRIN2 connected to an optical fiber F2 and which couples light into and out from the fiber cores C21, C22, C23 of the optical fiber F2. The coupling member has a distal end face OF2 optically connected to the proximal optical fiber end of the fiber F2, and a proximal end face IF2 spaced apart from the distal end in the longitudinal direction LC of the optical fiber F2.

The optical fiber F2 of the optical shape sensor OS may extend through the entire length of the guidewire GW in order to sense the optical shape of the guidewire in an interventional procedure. The optical fiber F2 may be a multi-core fiber having fiber cores C21, C22, C23. The optical fiber F2 may have more than three fiber cores, for example the optical fiber F2 may be configured like the optical fiber shown in FIGS. 2 and 3. In FIG. 4, the optical fiber core C22 is the central core with respect to the longitudinal axis LC of the fiber F2.

The optical connector part OC1 of the patch cord PC which in turn may be connected to the optical shape sensing console C as shown in FIG. 1 comprises an optical coupling member OCM1 which may be configured as a GRIN lens GRIN1 connected to an optical fiber F1 and which couples light into and out from the fiber cores C11, C12, C13 of the optical fiber F1. The coupling member has a distal end face OF1 and a proximal end face IF1 optically connected to the distal optical fiber end of the optical fiber F1. The connector part OC1 forms a counter-connector part to the connector part OC2.

FIG. 4 shows a typical case of a ¼ pitch GRIN lens GRIN2. The pitch will be explained later in more detail.

Light beams from each of the fiber cores C11, C12, C13 enter the GRIN lens GRIN1 at the proximal end face IF1 of the GRIN lens GRIN1, and exit the GRIN lens GRIN1 at the distal end face OF1 of the GRIN lens GRIN1 as collimated light beams. The collimation effect of the GRIN lens GRIN1 is due to the pitch of ¼ of the GRIN lens GRIN1. The collimated light beams then enter the optical connector part OC2 having the optical coupling member OCM2 here configured as the GRIN lens GRIN2 connected to the optical fiber F2. In FIG. 4, the whole arrangement of GRIN lens GRIN1 and GRIN lens GRIN2 has a pitch of ½. In view of the configuration of the GRIN lenses GRIN1 and GRIN2 as quarter pitch lens in each case, the set of collimated beams may enter and exit from connectors OC1 and OC2 to and from the focal points of the fiber cores C11, C12, C13 or C21, C22, C23 of the fibers F1, F2, and vice versa. It is to be noted that the light beam coming from fiber core C11 enters fiber core C23 after having propagated through the GRIN lenses GRIN1 and GRIN2, i.e. the image of the fiber cores C11, C12, C13 is inverted at the fiber cores C21, C22, C23.

GRIN lenses are a good choice in backloadable versions of optical shape sensing technologies in medical interventional devices because of their compactness and their principally low surface reflections. For, the light is not reflected or refracted at an air-glass transition, but bent in a graded index profile extending, for example, in the radial direction of the GRIN lens. This property is used to eliminate any air to glass transitions when the connection is established, i.e. when the optical fiber and GRIN lens are fusion spliced, glued or otherwise connected to one another. Between the connectors OC1 and OC2, a thin, index-matching intermediate layer IM, e.g. a foil, may be arranged to reduce or eliminate reflections at the distal end face OF1 of the GRIN lens GRIN1 and the proximal end face IF2 of the GRIN lens GRIN2. The same matching layer may have the mechanically favorable property of being deformable (compressible). In a general application, it may be a fluid or gel. Within the scope of the present invention and its application, it may be a foil that is elastic and compressible. In this way, the matching intermediate layer IM can morph to any surface irregularities of the connecting parts and provide a perfect mechanical and optical match between surfaces OF1 and IF2 of the optical coupling members OCM1 and OCM2.

FIG. 4 shows a typical length L of a GRIN lens of e.g. 1.3 mm and a typical diameter d of e.g. 0.3 mm. With reference to FIG. 5A to 5C, FIGS. 6A and 6B, the physical principals of GRIN lenses will be explained in more detail.

A GRIN lens or in general GRIN optical components have a gradual position dependent variation in the refractive index that is used to control the light propagation through the respective component. An important subset of GRIN optics consists of cylinders, also called GRIN rod lenses, with a refractive index that is changing only along the radial distance r. For example, GRIN rod lenses have a radial refractive index profile that is almost parabolic:

$$n(r) = n_0 \operatorname{sech}(gr) \approx n_o\left(1 - \frac{g^2 r^2}{2}\right), \quad (1)$$

where g is the gradient constant, $n_0$ is the refractive index in the center of the GRIN rod lens, and r is the radial position with respect to the longitudinal center axis of the GRIN rod lens. Light entering the GRIN rod lens is continuously refracted, and the optical field inside such a GRIN rod lens is therefore periodically changing along the z-axis (cylinder axis), with a period length of $$z_{period} = \frac{2\pi}{g}. \quad (2)$$

A common way to denote the length of a GRIN rod lens is in terms of the pitch P, which is the geometrical length L of the GRIN rod lens divided by the period length $z_{period}$:

$$P = \frac{L}{z_{period}} = \frac{Lg}{2\pi}. \quad (3)$$

According to equation (3), the geometrical length L of a GRIN lens is proportional to its pitch P.

Figure 5:
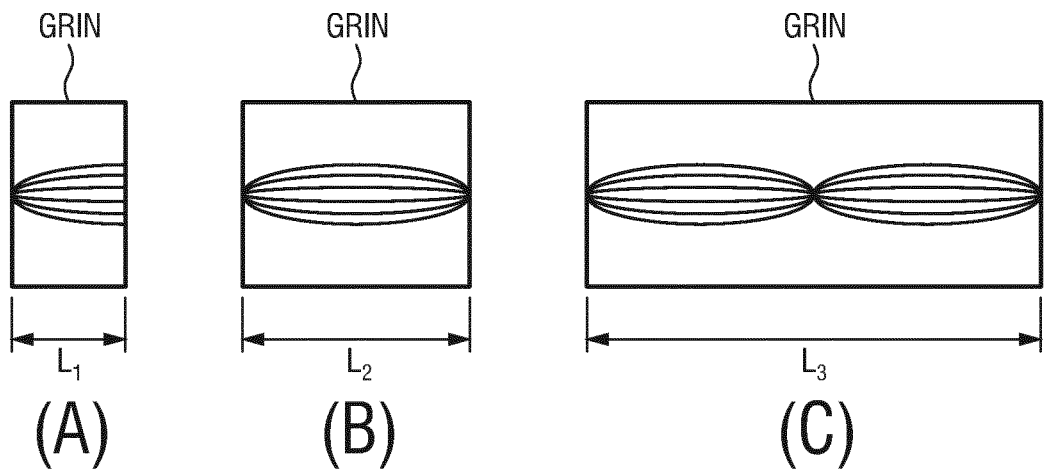
FIG. 5A-C show three GRIN lenses with different pitches.

FIG. 5A shows a GRIN rod lens with a pitch P=0.25, FIG. 5B shows a GRIN rod lens with a pitch P=0.5, and FIG. 5C shows a GRIN rod lens with a pitch P=1 in some examples.

A GRIN rod lens which has a pitch of P=1, 2, 3, 4, . . . , images its front plane onto its back plane and vice versa. GRIN rod lenses with of pitch of P=0.5, 1.5, 2.5, . . . , also image the front plane onto the back plane, but the image is now inverted, as it is the case with the GRIN lens arrangement in FIG. 4 formed by both GRIN lenses GRIN1 and GRIN2. Another typically used pitch is P=¼, ¾, 5⁄4, . . . , for which the GRIN rod lens collimates the light from every point on its front plane at its back plane, and vice versa.

Figure 6:
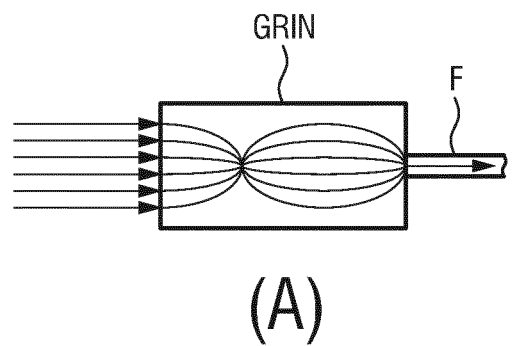
FIG. 6A, B show an optical fiber connected to GRIN lenses with different pitches.
Figure 6:
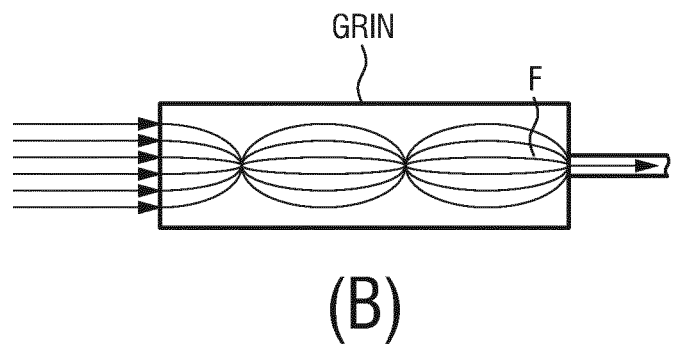
Figure 7:
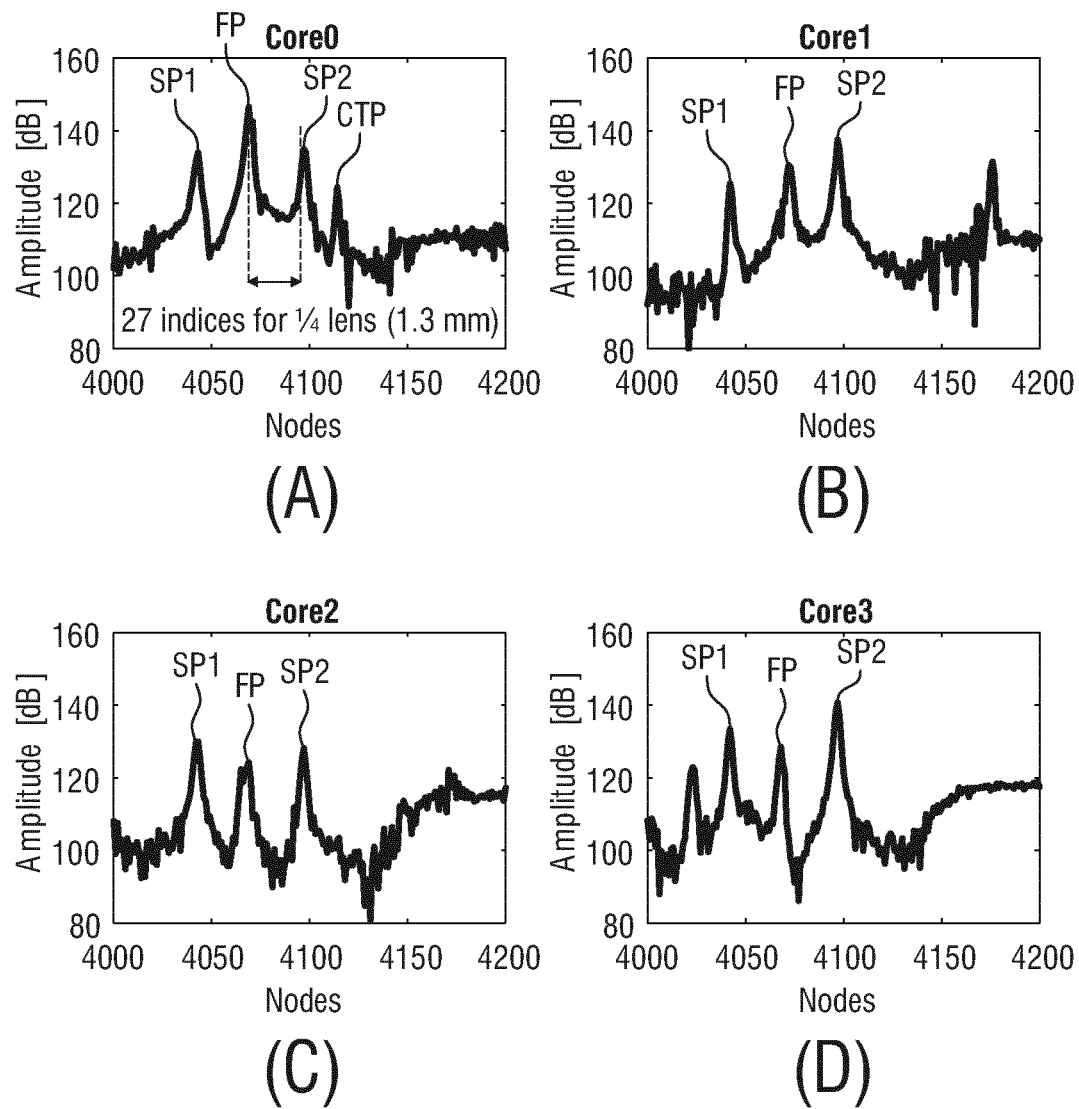
FIG. 7A-D show diagrams of intensities of optical response signals from four cores of an optical fiber.

FIG. 6A shows an example of a GRIN lens having a pitch of ¾, and FIG. 6B shows an example of a GRIN lens having a pitch of 5⁄4.

The numerical aperture of a GRIN rod lens is defined by the refractive index at the center of the GRIN rod lens and the refractive index at the outer boundary of the GRIN rod lens:

$$NA = n_0 \sqrt{1 - \mathrm{sech}^2\left(\frac{gd}{2}\right)}, \quad (4)$$

where d is the diameter of the GRIN rod lens perpendicular to the cylinder axis (see FIG. 1).

When the minimum required NA and the maximum diameter d is known, a GRIN rod lens may be designed with a gradient constant g according to the needs of the application:

$$g = \frac{2}{d} \mathrm{sech}^{-1}\left(\sqrt{1 - \left(\frac{NA}{n_0}\right)^2}\right). \quad (5)$$

When furthermore the required pitch P is known, the GRIN rod lens must have a length L as follows:

$$L = \frac{d\pi P}{\mathrm{sech}^{-1}\left(\sqrt{1 - \left(\frac{NA}{n_0}\right)^2}\right)}. \quad (6)$$

When making an optical connector like the optical connector OC2 of the shape sensor OS in FIG. 4, the fiber F2 and GRIN lens GRIN2 may be joined to one another by a fusion splicing process. Fusion splicing is a process by which the optical fiber F2 (FIG. 4) or F (FIG. 6A, 6B) and the GRIN lens GRIN2 (FIG. 4) or the GRIN lens GRIN (FIG. 6A, 6B) are joined end-to-end using heat. In other words, the optical fiber and the GRIN lens are fused together in that the material of the optical fiber and the GRIN lens is locally melted similar to a welding process. As an alternative method to join the optical fiber and the GRIN lens to one another is to use a thin layer of glue.

In optical shape sensing, strains are measured in the fiber cores C21, C22, C23 of the optical fiber F2 (FIG. 4) (or in the four cores 31, 32a, 32b, 32c of the optical fiber 30 (FIG. 2, 3)). Strain in the fiber cores may be due to bend and/or twist in the optical fiber. The optical shape sensing console C (FIG. 1) has an optical interrogation unit OIU which is configured to transmit input light into the fiber cores C21, C22, C23 of the optical fiber F2 of the optical shape sensor OS and to receive optical response signals from each of the fiber cores C21, C22, C23 (or 31, 32a, 32b, 32c) of the optical shape sensor OS in response to the input light. The optical response signals from each of the fiber cores are indicative of the strain in the optical fiber F2 along the optical shape sensor OS. The optical shape sensing control C further comprises a shape reconstruction unit SRU (FIG. 1) which is configured to reconstruct, by calculation, a shape of the optical shape sensor OS from the optical response signals received by the optical interrogation unit OIU. Optical shape sensing enables 3D-shape reconstruction of the optical shape sensor OS. Accurate shape reconstruction of the optical shape sensor OS requires a well-defined starting point or position along the optical shape sensor OS for the 3D-shape construction of the optical shape sensor OS down to the micron level. However, the optical response signals received from the fiber cores may have a relative delay in time from fiber core to fiber core, and it is difficult to recover the starting position for shape reconstruction for all the fiber cores from the optical response signals of the fiber cores. In other words, the response signals received from the fiber cores only provide relative starting positions that may differ from fiber core to fiber core. Therefore, some method is required to align these relative starting positions for all the fiber cores of the optical shape sensor OS down to the micron level in order to obtain a shape reconstruction of the optical shape sensor as accurate as possible.

One possibility to align the relative starting positions of the fiber cores could be to use a correlation method that uses the reflections from the fiber Bragg gratings in the optical fiber F2 or Rayleigh backscattering in the optical fiber F2. This method compares the present state of backscattering with previously recorded reflection profiles from perhaps several millimeters of fiber, as a calibration. This method, however, is disadvantageous because such a calibration requires that during the calibration process it is necessary to have a (temporary) physical marker that may be induced by, for example a pressure point, to precisely locate the relative physical location of the correlation sections of the different fiber cores. This method is also disadvantageous because it may be time-consuming.

Another possibility is to employ the reflection of the input light at the interface between the two GRIN lenses GRIN1 and GRIN2 in FIG. 4, i.e. the interface at the end faces OF1 of the GRIN lens GRIN1 and the end face IF2 of the GRIN lens GRIN2. This method has the advantage that it is independent of any calibration method. In this method, a refractive index step of glass-air-glass is the basis for the reflection at the optical interface between the GRIN lenses GRIN1 and GRIN2. This step occurs at exactly the same position for all fiber cores and alignments of the relative starting position may be easily obtained.

In the latter method, there are at least two problems however, one of which is based on the necessity to have a sterile barrier like the intermediate layer IM (FIG. 4), e.g. a foil, between the two connectors OC1 and OC2 of the patch cord PC and the guidewire GW when the latter is a backloadable guidewire. Further, at the interface between the two GRIN lenses GRIN1 and GRIN2 in FIG. 4, the reflected intensity of the input light may strongly vary due to contamination with blood, variable pressure on the connecting interface and due to the condition of the intermediate layer IM that is present to secure sterility of the connection of the two connectors OC1 and OC2 to one another. Another problem is that the end faces OF1 and IF2 may be not exactly polished at right angles to the optical axis so that a variable air gap may be present. These circumstances may hamper an accurate recovering of this interface in the optical response signals from the fiber cores, as will be explained below.

FIGS. 7A-D show an example of optical response signals received from four fiber cores Core0 to Core3 in an arrangement of FIG. 4 (with an optical fiber as shown in FIGS. 2 and 3) in response to input light, when a connection between two fibers F1 and F2 with ¼-pitch GRIN lenses GRIN1 and GRIN2 is made. Core0 denotes the central fiber core, and Core1, Core2, Core3 denote outer cores of the optical fiber F2.

FIG. 7A-D show for each of the fiber cores Core0, Core1, Core2, Core3 the amplitude distribution of the optical response signal of the corresponding fiber core along the optical connectors OC1 and OC2 (FIG. 4) (nodes 4000-4200 in the time-domain optical response signal). FP denotes a reflection peak of reflection of light at the optical interface between the two GRIN lenses GRIN1 and GRIN2 in FIG. 4, i.e. at the GRIN lens end faces OF1 and IF2 with the intermediate layer IM (foil) between them. A comparison between the reflection peaks FP among the fiber cores Core0, Core1, Core2, Core3 reveals that the reflection peak FP for the central core Core0 is higher, because the optical interface is at right angles to the central core Core0, and much of the reflected light is focused straight back into the fiber core Core0 of the optical fiber F1.

SP2 denotes a reflection peak of a reflection of light at the optical interface between the optical fiber F2 and the GRIN lens GRIN2 in FIG. 4, i.e. at the distal end face OF2 of the GRIN lens GRIN2. As shown for the fiber core Core0, the reflection peaks FP and SP2 are separated from one another by about 27 indices (nodes) in the case of GRIN lens GRIN2 that is a ¼-pitch GRIN lens. As can also be taken from FIG. 7A-D, the reflection peaks SP2 are higher than the reflection peaks FP for the outer cores Core1-Core3, while the reflection peak SP2 is lower than the reflection peak FP for Core0.

SP1 denotes a reflection peak of a reflection of light at the optical interface between the optical fiber F1 and the GRIN lens GRIN1 in FIG. 4, i.e. at the proximal end face IF1 of the GRIN lens GRIN1. CTP denotes a peak of the amplitude distribution of the optical response signal due to cross-talk from the outer cores into the central core Core0.

It appears from FIGS. 7A-D that, for a backloadable optical shape sensor OS, the reflection at the optical interface between the optical fiber F2 and the GRIN lens GRIN2 may be useful for serving as a common starting position for all fiber cores for shape reconstruction. This means, it is possible to measure the time position of the light reflections at the optical interface at the transition from the GRIN lens GRIN2 to the optical fiber F2 of the optical shape sensor OS and adjust the time delay between the fiber cores to zero. At that point, the reflections at that optical interface are or can be made to be mild, but well visible and stable.

However, the tails of the reflected intensity distribution of reflections at the interface between the two GRIN lenses GRIN1 and GRIN2 can overlap the reflection intensity distribution of the reflection at the optical interface between the optical fiber F2 and the GRIN lens GRIN2 deteriorating the accuracy of position (which, in a typical system, should be approximately 0.02 of a node distance or 1 micron propagation delay) with which the reflection peak SP2 can be measured. This overlap may thus prevent accurate recovering of the starting position for each of the fiber cores of the optical fiber F2 from the reflection peaks SP2 from the optical interface between the optical fiber F2 and the GRIN lens GRIN2.

Therefore, according to the present invention, the partially reflective and substantially transmissive optical interface at the transition from the GRIN lens GRIN2 to the proximal fiber end of the optical fiber F2 should be arranged in such a distance distally from the proximal end face IF2 of the GRIN lens GRIN2 and be configured such that light is reflected at the optical interface at the transition from the GRIN lens GRIN2 to the optical fiber F2 with a reflection intensity distribution which substantially does not overlap with the reflection intensity distribution of light reflected at the proximal end face IF2 of the GRIN lens GRIN2.

According to principles of the present invention, the length of the GRIN lens GRIN2 is enlarged to pull the reflection peaks FP and SP2 farther apart from one another. However, in a backloadable version of a shape sensing enabled guidewire GW, the GRIN lens GRIN2 must have a small diameter. Given a numerical aperture of the optical fiber F2 of typically NA=0.21 and a typical field diameter of 70 micron for a 125 micron optical fiber sensor, this requires a rather small focal length (quarter pitch length) of 1.0-1.5 mm so that the light may be collimated within a 0.25-0.40 mm diameter for all fiber cores with sufficiently low GRIN lens aberrations. These parameters are compatible with most widely utilized guidewire diameters of 0.36 mm, 0.46 mm, or 0.89 mm.

Therefore, for a given situation, lengthening of the GRIN lens GRIN2 should be done without changing the numeral aperture and radial cross section of the GRIN lens GRIN2. According to the present invention, this can be accomplished by using higher pitch lenses such as ¾- and ⁵⁄₄-pitch GRIN lenses that also produce a collimated beam. Such GRIN lenses are a very good compromise between GRIN lens aberrations and a sufficient separation of the reflection peaks FP and SP2 wherein the latter provides a more accurate recovery of the relative starting positions for each fiber core for shape reconstruction and for alignment of these relative starting positions to find a common starting position for shape reconstruction.

Figure 8:
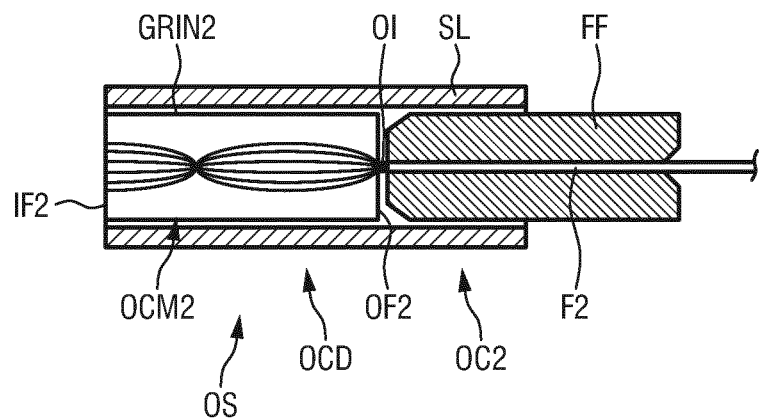
FIG. 8 shows an embodiment of an optical fiber and GRIN lens arrangement according to an embodiment of the invention.

FIG. 8 shows an embodiment of an optical shape sensor OS which is configured according to the principles of the present invention. The optical shape sensor OS comprises an optical connector OC2 having a GRIN lens GRIN2 of ¾ pitch. In this way, an optical interface OI at the transition from the proximal end of the optical fiber F2 to the distal end face OF2 of the GRIN lens GRIN2 is in a sufficient distance distally from the proximal end face IF2 of the GRIN lens GRIN2 so that a reflection peak SP2 of a reflection intensity distribution at the optical interface OI is well separated from a reflection peak FP of a reflection intensity distribution at the proximal end face IF2 of the GRIN lens GRIN2. Also shown in FIG. 8 is a fiber ferrule FF accommodating the optical fiber F2 and a tube or sleeve SL accommodating the fiber ferrule FF and the GRIN lens GRIN2 in a mechanical stable manner.

The optical fiber F2 may be fusion spliced to the GRIN lens GRIN2. In this case, the fusion splice may form the optical interface OI. A gradient-index transition layer may be formed as a result of the fusion-splicing process in which the glass material of lens and fiber are joined. The thickness of this layer may typically be 10 nm-100 nm, or even more, depending on the exact procedure. A layer of this kind will generally reduce the reflected intensity.

To good approximation, the reflection of a sharp transition between a GRIN lens of refractive index $n_0 = 1.472$ and an optical fiber with mode refractive index $n_{mode} = 1.451$ is given by:

$$R \approx \left( \frac{n_0 - n_{mode}}{n_0 + n_{mode}} \right)^2$$

For the given values this leads to a reflection of $R = 5.1 \times 10^{-5}$, which is rather high for the purpose of this invention. Using the advantage of a gradient-index transition layer one can reduce the reflection further by a factor of 10-100, and in a practical situation a factor of approximately 50 is found.

If the optical fiber F2 is connected to the GRIN lens GRIN2 by gluing them to one another, the optical interface OI may be formed by a layer of adhesive or glue. It is also possible to use the GRIN lens in FIG. 6B having a pitch of ⅝ as the GRIN lens GRIN2, or GRIN lenses of even higher odd-quarter pitch may be used as the lens GRIN2, if GRIN lens aberrations are not too high.

In general, a ratio of an intensity of light reflected at the optical interface OI to an intensity of light incident onto the optical interface OI may be in a range from $10^{-6}$ to $10^{-5}$.

Figure 9:
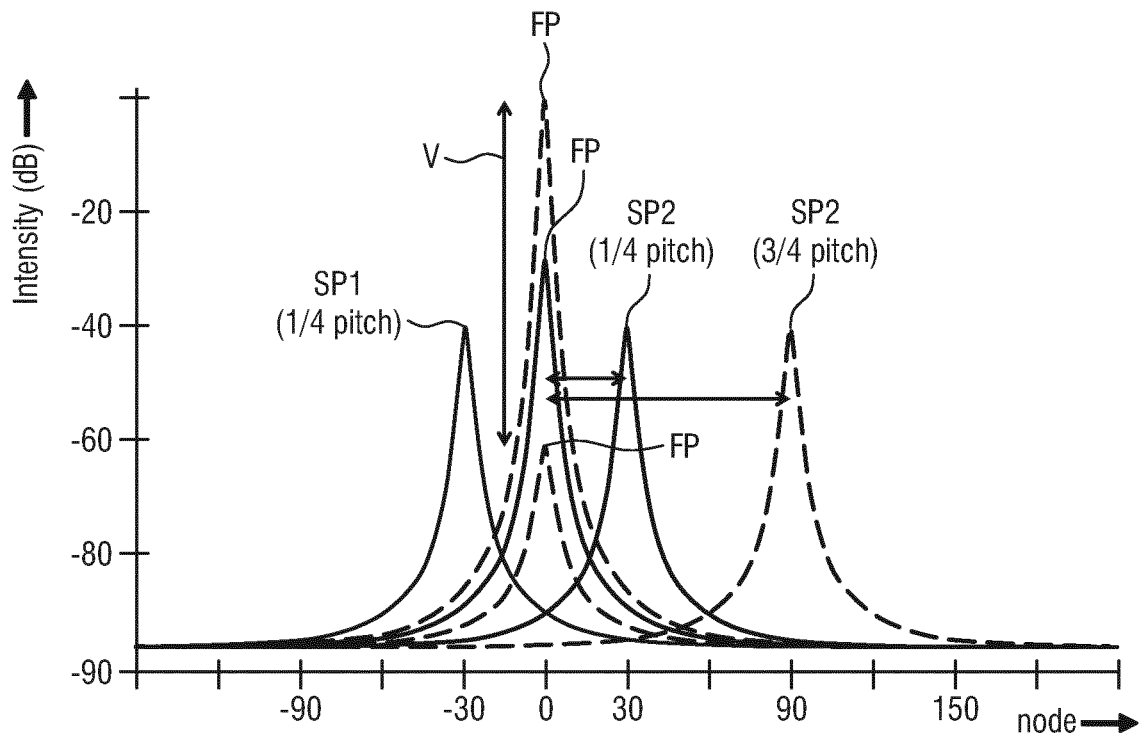
FIG. 9 shows a diagram of a reflection intensity distribution in the time-domain from an optical fiber/GRIN lens arrangement according to FIG. 4 with a ¼ pitch GRIN lens and with a ¾ pitch GRIN lens on the shape sensor side.

FIG. 9 shows the optical response signals in the time-domain from the arrangement in FIG. 4 for a ¼-pitch GRIN lens GRIN2 and a ¾-pitch GRIN lens GRIN2. The reflection peak FP from the optical interface between the two GRIN lenses GRIN1 and GRIN2 and that from the optical interface at the transition from the optical fiber F2 to the GRIN lens GRIN2 do overlap substantially if the GRIN lens GRIN2 is a ¼-pitch GRIN lens. The situation is much better in case of the arrangement according to FIG. 8 which uses a ¾-pitch GRIN lens GRIN2.

The advantageous effect of the optical shape sensor OS according to FIG. 8 is that, as shown in FIG. 9, the tail of the reflection peak FP of light reflected at the interface between the two GRIN lenses GRIN1 and GRIN2 has much less overlap with the reflection intensity distribution around peak SP2 of light reflected at the optical interface OI for the ¾-pitch GRIN lens GRIN2 in comparison with a GRIN lens having a ¼-pitch ("SP2 (¼-pitch)" in FIG. 9). The reflection peak SP2 (¾-pitch) is shifted by a factor of 3 from the reflection peak FP in comparison with the reflection peak SP2 (¼-pitch). As shown by an arrow V in FIG. 9, the reflection peak FP is variable and unpredictable (depending on compression, blood contamination of the foil, etc.) and therefore its effect cannot easily be adjusted for. This is for example different from the situation with the signal from the fiber Bragg gratings, which is predictable and can be filtered away.

The reflection peak SP1 at the optical interface between the optical fiber F1 and the GRIN lens GRIN1 having a pitch of ¼ is also shown in FIG. 9. Use of a higher pitch GRIN lens GRIN1 is not necessary because the reflection peak SP1 is even farther separated from the reflection peak SP2 (¾-pitch) than the reflection peak FP.

Thus, by using a ¾-pitch GRIN lens GRIN2, the influence of the reflection peak FP from reflections at the interface between the two GRIN lenses GRIN1 and GRIN2 on the reflection peak SP2 from reflections at the optical interface OI is reduced and thus the position of the peaks SP2 for each fiber core C21-C23 (or 31, 32a, 32b, 32c) can be measured with lower background intensity and thus more accurately.

Figure 10:
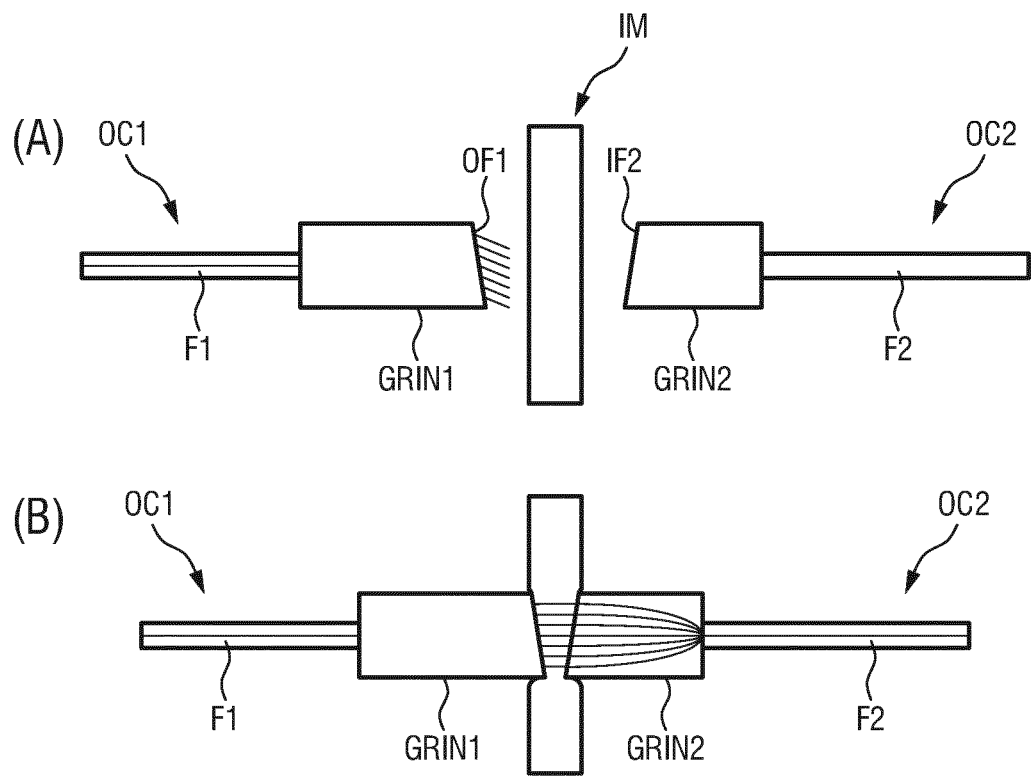
FIG. 10A, B show two optical fibers each connected to a GRIN lens together with an intermediate layer between the two GRIN lenses.

The accuracy of the reflection peak position determination of the reflection peak SP2 for a ¾-pitch or ⅝-pitch GRIN lens GRIN2 can be further improved by increasing the height of the reflection peak SP2 with respect to the reflection peak FP. This can be achieved by lowering the reflection peak FP by using an index-matched optimized intermediate layer IM or by polishing the end faces OF1 and IF2 of the GRIN lenses GRIN1 and GRIN2 in FIG. 4 under a small angle, as shown in FIGS. 10A and B. The layer IM, e.g. a foil, may be thick and compressive enough to overcome the geometrical differences introduced by the angle polish of the end faces OF1 and IF2. Without the foil IM the light would exit the GRIN lens GRIN1 under an angle due to the angle polish of the end face OF1. Because the orientation of the angle polish may not be identical in both lenses GRIN1 and GRIN2, a proper optical connection between the lenses would not be possible. By using the compressible foil IM in between the two lenses GRIN1 and GRIN2, the light exits straight again towards the second GRIN lens GRIN2. In this way, the compressible foil enables a proper connection without requiring that the angle polish on both GRIN lenses GRIN1 and GRIN2 is oriented in the same way. The foil IM may be index-matched to reduce the reflection of light at the end face IF2 of the GRIN lens GRIN2.

An alternative or an additional measure is to increase the reflection peak SP2, which can be done by tuning the refractive index difference between the GRIN lens GRIN2 and the optical fiber F2, for example by choosing materials for these elements which have sufficiently different refractive indices to provide a sufficient refractive index step at the optical interface OI, for the fusion splice version (see examples for $n_0$ and $n_{mode}$ above), or, in case that the optical fiber F2 and the GRIN lens GRIN2 are glued together, by using an appropriate glue providing a sufficient refractive index step at the optical interface OI. In general, an optical interface refractive index of the optical interface OI may be different from at least one of an optical fiber refractive index of the optical fiber F1 and an optical coupling member refractive index of the optical coupling member OCM2.

With reference to FIG. 1 again, the optical interrogation unit OIU is configured to transmit input light into the optical shape sensor OS and to receive optical response signals from each of the fiber cores (e.g. C21, C22, C23) of the optical shape sensor OS in response to the input light. The received light for each channel or fiber core is measured as output from an interferometer, and hence both the phase and intensity are measured. The shape reconstruction unit SRU is configured to reconstruct a shape of the optical shape sensor OS from the optical response signals, wherein the shape reconstruction unit SRU is configured to determine a starting position for each of the fiber cores of the optical shape sensor for shape reconstruction from the optical response signals. The shape reconstruction unit SRU is configured to identify or measure a respective peak SP2 of the reflection intensity distribution of reflections at the optical interface OI at the transition from the optical fiber F2 to the GRIN lens GRIN2 as described above in the optical response signals and to determine the relative starting positions of each of the fiber cores for the shape reconstruction from these peaks.

The shape reconstruction unit SRU may be further configured to align the starting positions of the fiber cores for the shape reconstruction, for example using a phase recovery algorithm for the interferometric signals of each channel to align the identified starting positions of the fiber cores for the shape reconstruction.

In a method of optical shape sensing, input light is transmitted into the optical shape sensor OS, and optical response signals are received from each of the fiber cores (e.g. fiber cores C21, C22, C23) of the optical shape sensor OS in response to the input light. The shape of the optical shape sensor OS is reconstructed from the optical response signals. A respective peak of a reflection intensity distribution of light reflected at the optical interface OI (FIG. 4, 8) is identified in the optical response signals. A shape reconstruction starting position for each of the fiber cores is determined from the peaks, and a shape of the optical shape sensor starting from the shape reconstruction starting position is reconstructed.

The method may be performed by a computer program comprising program code means for causing a computer to carry out the method as mentioned before, when said computer program is carried out on a computer.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An optical shape sensor, comprising
an optical fiber having a length defining a longitudinal direction, the optical fiber having at least two fiber cores extending along the length of the optical fiber;
an optical coupling member comprising a graded refractive index (GRIN) lens and arranged at a proximal optical fiber end of the optical fiber, the coupling member having a first distal end face optically connected to the proximal optical fiber end, and a proximal second end face spaced apart from the first distal end face in the longitudinal direction of the optical fiber, the optical coupling member being configured to couple light into each of the fiber cores; and
an optical interface (OI) at a transition from the optical coupling member to the proximal optical fiber end, the optical interface (OI) being partially reflective and substantially transmissive, wherein the optical interface (OI) is arranged in such a distance distally from the proximal second end face and is configured such that light is reflected at the optical interface (OI) with a reflection intensity distribution which substantially does not overlap in time with a reflection intensity distribution of light reflected at the second end face of the optical coupling member, wherein the optical interface (OI) marker reflection has a greater amplitude than a shape sensing signal from the optical shape sensor so that it is clearly discernible.

2. The optical shape sensor of claim 1, wherein the GRIN lens has a pitch of k/4, wherein k is an odd integer greater than or equal to 1.

3. The optical shape sensor of claim 2, wherein k is 3, 5, or 7.

4. The optical shape sensor of claim 1, wherein an optical interface refractive index of the optical interface (OI) is different from at least one of an optical fiber refractive index of the optical fiber and an optical coupling member refractive index of the optical coupling member.

5. The optical shape sensor of claim 1, wherein the distal first end of the optical coupling member is fusion spliced to the proximal optical fiber end, and the optical interface (OI) is provided at the fusion splice.

6. The optical shape sensor of claim 1, wherein the distal first end of the optical coupling member is connected to the proximal optical fiber end via a glue layer, and the optical interface (OI) is provided at the glue layer.

7. The optical shape sensor of claim 1, wherein a ratio of an intensity of light reflected at the optical interface (OI) to an intensity of light incident onto the optical interface (OI) is in a range from $10^{-6}$ to $10^{-5}$.

8. The optical shape sensor of claim 1, wherein the proximal end face of the optical coupling member is configured to be connected to a distal end of a light supplying patch cord (PC) supplying input light, wherein a foil is arranged at the proximal end face of the optical coupling member which is configured to reduce a reflection of light at the connection of the proximal end face of the optical coupling member and the distal end of the light supplying patch cord.

9. An optical shape sensing console, comprising
an optical interrogator configured to transmit input light into an optical shape sensor (OS) according to claim 1 and to receive optical response signals from each of the fiber cores of the optical shape sensor (OS) in response to the input light,
a shape reconstructor configured to reconstruct a shape of the optical shape sensor (OS) from the optical response signals, wherein the shape reconstructor is configured to determine a starting position for shape reconstruction for each of the fiber cores from the optical response signals, wherein the shape reconstructor is configured to identify a respective peak of a reflection intensity distribution of input light reflected at the optical interface (OI) in the optical response signals of the fiber cores and to determine a respective starting position for shape reconstruction from said peaks.

10. The optical shape sensing console of claim 9, wherein the shape reconstructor is further configured to align the determined starting positions for the fiber cores with respect to one another.

11. The optical shape sensing console of claim 10, wherein the shape reconstructor is configured to use a phase recovering algorithm to align the determined starting positions.

12. The optical shape sensing system, comprising an optical shape sensor (OS) and an optical shape sensing console (C) according to claim 9.

13. A method of optical shape sensing, comprising
- transmitting input light into an optical shape sensor comprising an optical fiber having a length defining a longitudinal direction, the optical fiber having at least two fiber cores extending along the length of the optical fiber,
- an optical coupling member comprising a GRIN lens arranged at a proximal optical fiber end of the optical fiber, the coupling member comprising the GRIN lens having a first distal end face optically connected to the proximal optical fiber end, and a proximal second end face spaced apart from the first distal end face in the longitudinal direction of the optical fiber, the optical coupling member being configured to couple light into each of the fiber cores,
- an optical interface (OI) at a transition from the optical coupling member to the proximal optical fiber end, the optical interface (OI) being partially reflective and substantially transmissive, wherein the optical interface (OI) is arranged in such a distance distally from the proximal second end face and is configured such that light is reflected at the optical interface (OI) with a reflection intensity distribution which substantially does not overlap in time with a reflection intensity distribution of light reflected at the second end face of the optical coupling member comprising the GRIN lens,
- receiving optical response signals from each of the fiber cores of the optical shape sensor (OS) in response to the input light,
- identifying a respective peak of a reflection intensity distribution of input light reflected at the optical interface (OI) in the optical response signals,
- determining a shape reconstruction starting position for each of the fiber cores from the peaks, and
- reconstructing a shape of the optical shape sensor (OS) starting from the shape reconstruction starting position.

14. A tangible, non-transitory computer readable medium that stores instructions, which when executed by a processor, cause the processor to:
- transmit input light into an optical shape sensor comprising an optical fiber having a length defining a longitudinal direction, the optical fiber having at least two fiber cores extending along the length of the optical fiber, wherein: an optical coupling member is arranged at a proximal optical fiber end of the optical fiber, the coupling member having a first distal end face optically connected to the proximal optical fiber end, and a proximal second end face spaced apart from the first distal end face in the longitudinal direction of the optical fiber, the optical coupling member being configured to couple light into each of the fiber cores; an optical interface (OI) is disposed at a transition from the optical coupling member to the proximal optical fiber end, the optical interface (OI) being partially reflective and substantially transmissive; and the optical interface (OI) is arranged in such a distance distally from the proximal second end face and is configured such that light is reflected at the optical interface (OI) with a reflection intensity distribution which substantially does not overlap in time with a reflection intensity distribution of light reflected at the second end face of the optical coupling member;
- receive optical response signals from each of the fiber cores of the optical shape sensor (OS) in response to the input light;
- identify a respective peak of a reflection intensity distribution of input light reflected at the optical interface (OI) in the optical response signals;
- determine a shape reconstruction starting position for each of the fiber cores from the peaks; and
- reconstruct a shape of the optical shape sensor (OS) starting from the shape reconstruction starting position.

\* \* \* \* \*